United States Patent
Hsu et al.

(10) Patent No.: US 10,011,575 B2
(45) Date of Patent: Jul. 3, 2018

(54) METHOD FOR FABRICATING TITANIUM-CONTAINING SILICON OXIDE MATERIAL AND APPLICATION OF THE SAME

(71) Applicant: ORIENTAL UNION CHEMICAL CORP., Kaohsiung (TW)

(72) Inventors: Yu-Chuan Hsu, Kaohsiung (TW); Chia-Yao Tseng, Kaohsiung (TW); Po-Sung Wu, Kaohsiung (TW); Hsi-Chin Tsai, Kaohsiung (TW)

(73) Assignee: Oriental Union Chemical Corp., Kaohsiung (TW)

( * ) Notice: Subject to any disclaimer, the term of this patent is extended or adjusted under 35 U.S.C. 154(b) by 1 day.

(21) Appl. No.: 15/218,710

(22) Filed: Jul. 25, 2016

(65) Prior Publication Data

US 2018/0022720 A1     Jan. 25, 2018

(51) Int. Cl.

| | |
|---|---|
| *B01J 21/06* | (2006.01) |
| *C07D 301/19* | (2006.01) |
| *B01J 21/08* | (2006.01) |
| *B01J 37/04* | (2006.01) |
| *B01J 37/02* | (2006.01) |

(52) U.S. Cl.
CPC ............ *C07D 301/19* (2013.01); *B01J 21/08* (2013.01); *B01J 37/0236* (2013.01); *B01J 37/04* (2013.01)

(58) Field of Classification Search
CPC ..... C07D 301/19; B01J 34/0236; B01J 34/04; B01J 21/08

USPC .......................................... 549/529; 502/242
See application file for complete search history.

(56) References Cited

U.S. PATENT DOCUMENTS

| | | | | |
|---|---|---|---|---|
| 3,923,843 | A * | 12/1975 | Wulff ..................... | B01J 21/063 549/529 |
| 4,833,260 | A * | 5/1989 | Neri ....................... | B01J 29/035 549/531 |
| 6,512,128 | B2 | 1/2003 | Yamamoto et al. | |
| 6,881,697 | B1 | 4/2005 | Stocker | |
| 6,887,823 | B2 | 5/2005 | Yamamoto et al. | |
| 7,018,950 | B2 | 3/2006 | Yamamoto | |
| 2007/0260074 | A1* | 11/2007 | Buijink ................. | B01J 21/063 549/529 |

FOREIGN PATENT DOCUMENTS

| | | | |
|---|---|---|---|
| CA | 1265810 | * | 2/1990 |
| CN | 103861574 B | | 11/2015 |

* cited by examiner

*Primary Examiner* — Taylor V Oh
(74) *Attorney, Agent, or Firm* — Muncy, Geissler, Olds & Lowe, P.C.

(57) ABSTRACT

A method for fabricating a titanium-containing silicon oxide material and an application of the same are disclosed. The method needn't use a template but directly use an amorphous silicon dioxide and a titanium source as the reactants. The reactants are mixed with a solvent and react in the solvent. The suspension generated by the reaction is processed by solid-liquid separation, flushing and drying to obtain a titanium-containing silicon oxide material. The method features a simplified fabrication process and a low fabrication cost. The titanium-containing silicon oxide material fabricated by the method has a superior catalytic activity, able to catalyze an epoxidation reaction of an olefin-group compound to generate an epoxide.

15 Claims, 2 Drawing Sheets

METHOD FOR FABRICATING TITANIUM-CONTAINING SILICON OXIDE MATERIAL AND APPLICATION OF THE SAME

BACKGROUND OF THE INVENTION

Field of the Invention

The present invention relates to a method for fabricating a titanium-containing silicon oxide material and an application of the same, particularly to a method for synthesizing a titanium-containing silicon oxide material without using templates and an application using the titanium-containing silicon oxide material as a catalyst to directly oxidize olefin into an epoxide.

Description of the Related Art

Titanium-containing silicon oxide materials normally have porous structure with large surface area, able to function as a superior absorptive agent, a catalyst or a catalyst carrier. At present, the synthesis of titanium-containing silicon oxide materials usually adopts a hydrothermal reaction method and uses a surfactant as the template agent. The most well-known example of the abovementioned template is a positively-charged quaternary ammonium salt surfactant. U.S. Pat. No. 7,018,950, U.S. Pat. No. 6,887,823 and U.S. Pat. No. 6,512,128 disclosed methods for fabricating titanium-containing silicon oxide catalysts, which are characterized in the following steps: mixing and agitating a silicon source, a titanium source and a quaternary ammonium salt (functioning as the template) in a solvent to obtain a solid material containing a catalyst material and a template material; using a solvent-extraction method to remove the template material from the solid material and obtain a titanium-containing catalyst having specified pore diameters, a specified pore diameter distribution, and a specified volume ratio.

In the process of the abovementioned conventional technology, the template agent forms micro-bubbles in the water solution; the added silicon compound aggregates around the micro-bubbles and forms a silicon oxide substrate; a high-temperature calcination process is usually used to remove the template agent (i.e. the surfactant) and generate pores whose size and shape is similar to that of the template agent. The advantages of the abovementioned process are that the volume of the pores of the synthesized material can be modified with the molecular size of the template agent and that the size of the pores can be regulated with the size of the micro-bubbles of the template agent. However, the template agent may be toxic and harmful to the environment.

The sol-gel method is another common method to fabricate titanium-containing silicon oxide materials. For an example, a China patent No. CN103861574 disclosed a method for fabricating a titanium-silicon complex oxide, which is characterized in the following steps: adding a template agent to an inorganic titanium source and an inorganic silicon source; using a sol-gel method, together with a neutralization process, a weathering process, a flushing process and a calcination process to obtain a titanium-silicon complex oxide. For another example, a U.S. Pat. No. 6,881,697 disclosed a method for fabricating a titanium-containing silicon oxide catalyst, which includes steps: gelatinizing a silicon compound and a titanium alkoxy compound in a solvent of water, alcohol, or water plus alcohol; and passing a supercritical fluid through the gel to remove the solvent in the gel. Gelatinization of a silicon compound and a titanium alkoxy compound in a solvent of water, alcohol, or water plus alcohol can be realized via adding an acid or base functioning as a promoter into a water solution, an alcohol solution or a water-alcohol solution of a silicon compound and a titanium compound to enable a hydrolysis-condensation reaction of the silicon compound and the titanium compound to obtain a polymeric condensate gel containing Si—C—Si bonds, Si—O—Si bonds, and Si—O—Ti bonds. No matter whether a template agent is used, the process of the sol-gel method is more complicated and harder to control the shape and size of the titanium-containing silicon oxide particles. Thus, the titanium-containing silicon oxide material fabricated with the sol-gel method has a lower catalytic activity.

In order to overcome the abovementioned problems, the Inventor develops a method for fabricating a titanium-containing silicon oxide material and an application of the same. The method is exempted from using a template agent, having a simplified fabrication process and a lower fabrication cost. Further, the titanium-containing silicon oxide material fabricated by the method has a high catalytic activity in an epoxidation reaction.

SUMMARY OF THE INVENTION

The primary objective of the present invention is to provide a method for fabricating a titanium-containing silicon oxide material and an application of the same. The method is characterized in fabricating a titanium-containing silicon oxide material having a high catalytic activity without using a template agent, wherein an amorphous silicon dioxide, a titanium source and a solvent are mixed to form a mixture liquid; the mixture liquid reacts to form a product; the product is filtered and dried to obtain a titanium-containing silicon oxide material having a high catalytic activity and functioning as a catalyst to catalyze an epoxidation reaction of olefin and generate an epoxide.

In order to achieve the abovementioned objective, the present invention proposes a method for fabricating a titanium-containing silicon oxide material, which comprises steps: mixing an amorphous silicon dioxide, a titanium source, and a solvent to form a mixture solvent; undertaking a reaction of the mixture liquid at a temperature of 20-100° C. for 0.5-3 hours; undertaking a solid-liquid separation process; drying the solid obtained from the solid-liquid separation process to generate a titanium-containing silicon oxide material. In an anhydrous state, the titanium-containing silicon oxide material is expressed by Formula (I):

$$x\text{TiO}_2(1-x)\text{SiO}_2 \qquad (I)$$

wherein x is a number within 0.002-0.2.

The abovementioned amorphous silicon dioxide has a general formula: $SiO_2$, selected from a group including smoked silica, fumed silica, silica gel, and silica sol. The titanium source may be a titanate or an inorganic titanium source. The solvent may be an alcohol-group compound, wherein the alcohol is referred to an alcohol having 1-10 carbon atoms, such as methyl alcohol, ethyl alcohol, isopropyl alcohol, butyl alcohol, and tert-butyl alcohol.

The present invention also proposes a method for fabricating an epoxide, wherein the titanium-containing silicon oxide material fabricated by the abovementioned method is used as the catalyst to enable the reaction of olefin and oxide to form an epoxide.

In one embodiment, calcination and/or silylation is undertaken to enhance the catalytic activity of the catalyst before the catalyzed reaction.

In the present invention, the quantity of the catalyst used in the method for fabricating an epoxide is not strictly limited as long as the epoxidation reaction can be fully completed. In the method for fabricating an epoxide, the molar ratio of olefin to oxide ranges from 1:100 to 100:1, preferably 1:10 to 10:1. The present invention does not particularly limit the reaction temperature of the method for fabricating an epoxide. The reaction temperature is normally within 0-200° C., preferably within 25-150° C. The present invention does not particularly limit the reaction pressure of the method for fabricating an epoxide as long as the pressure is sufficient to maintain all the reactants in a liquid state. The reaction pressure is preferably within 1-100 atm. In the present invention, the reaction time of the method for fabricating an epoxide is from 1 minute to 48 hours, preferably from 5 minutes to 8 hours. The method for fabricating an epoxide of the present invention can be undertaken in batches, continuously, or semi-continuously in various types of reactors and instruments, such as fixed bed reactors, transport bed reactors, fluid bed reactors, slurry reactors, and continuously-stirred tank reactors.

The methods of the present invention feature simplified processes and low fabrication cost. The catalyst fabricated by the present invention has a superior catalytic activity. Therefore, the present invention is very useful in the industry.

Below, embodiments are described in detail to make easily understood the objectives, technical contents, characteristics and accomplishments of the present invention.

DETAILED DESCRIPTION OF THE INVENTION

Figure 1:
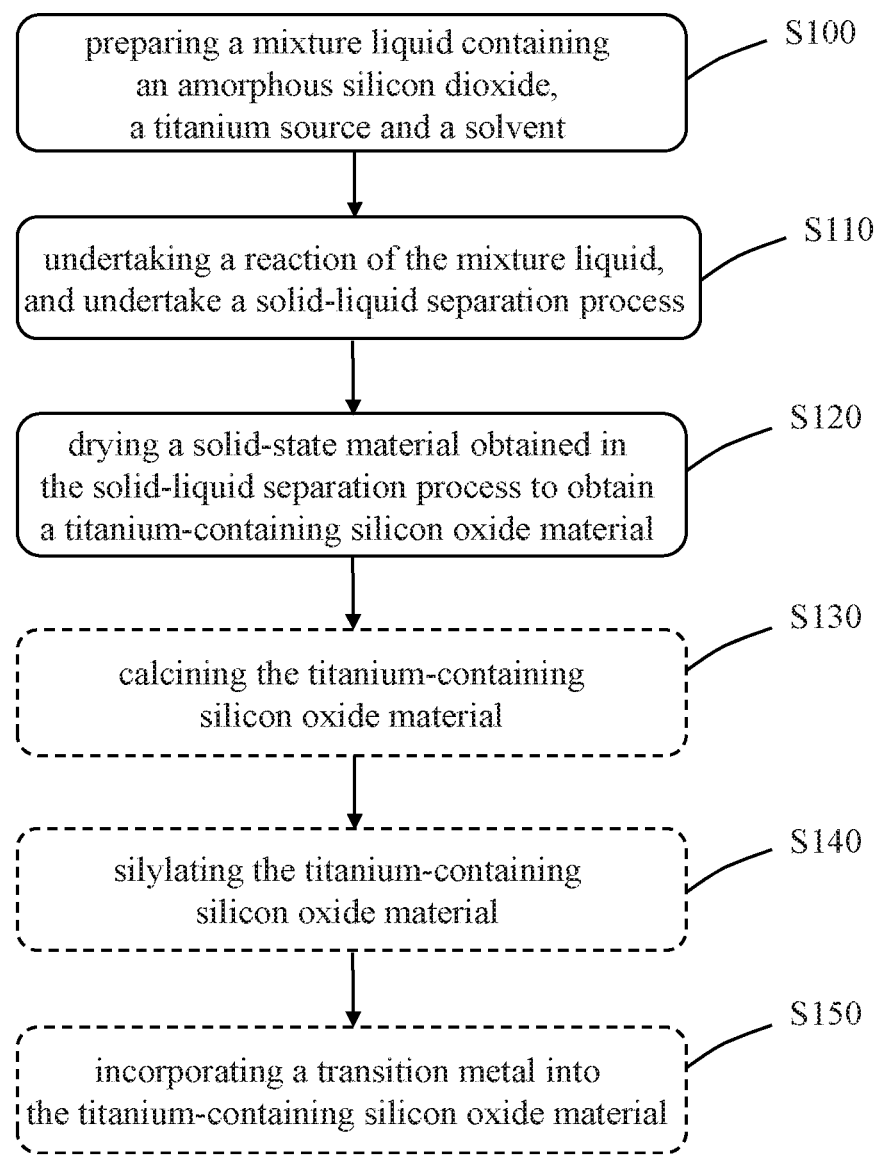
FIG. 1 is a flowchart of a method for fabricating a titanium-containing silicon oxide material according to one embodiment of the present invention.

Refer to FIG. 1 a flowchart of a method for fabricating a titanium-containing silicon oxide material according to one embodiment of the present invention. There are six steps in the flowchart of FIG. 1, including Steps S100-S150. Step S100, Step S110 and Step S120 describe the procedures to fabricate a titanium-containing silicon oxide material. Step S130, Step S140 and Step S150 are the steps that may be added to the process of fabricating a titanium-containing silicon oxide material to obtain a titanium-containing silicon oxide material having a high catalytic activity. In practical application, a single fabrication process can adopt one or more of Step S130, Step S140, and Step S150. However, the three optional steps are jointly presented in a single flowchart to simplify the diagram, and the dash-line frames indicate that the steps are optional.

In Step S100, mix an amorphous silicon dioxide, a titanium source and a solvent to form a mixture liquid. In practical operation, Step S100 can be realized in the following ways: the first way: directly mixing the silicon oxide, the titanium source and the solvent to form the mixture liquid; the second way: mixing the titanium source and the solvent to form Solution A, and mixing the silicon dioxide with Solution A to form the mixture solution; the third way: mixing the titanium source to form Solution A, and mixing the silicon dioxide with the solvent to form Solution B, and then mixing Solution A and Solution B to form the mixture liquid.

The silicon dioxide used in the present invention has a general formula: $SiO_2$. The silicon dioxide may be but is not limited to be selected from a group including smoked silica, fumed silica, silica gel, and silica sol. The titanium source used in the present invention may be but is not limited to be a titanate or an inorganic titanium source. The titanate may be but is not limited to be selected from a group including tetramethyl titanate, tetraethyl titanate, tetrapropyl orthotitanate, tetra isopropyl titanate, tetrabutyl orthotitanate, tetra sec-butyl titanate, tetrabutyl isotitanate, tetra tert-butyl titanate, and combinations thereof. The inorganic titanium source may be a titanium halide, such as titanium trichloride or titanium tetrachloride, or a combination of different titanium halides. The solvent may be an alcohol-group compound, wherein the alcohol is referred to an alcohol having 1-10 carbon atoms, such as methyl alcohol, ethyl alcohol, isopropyl alcohol, butyl alcohol, tert-butyl alcohol, or a combination thereof.

In the mixture liquid, the molar ratio of titanium to silicon ranges from 0.002 to 0.2, preferably 0.01 to 0.1. The present invention does not particularly limit the quantity of the solvent as long as the silicon dioxide material can be agitated in the solvent.

In Step S110, undertake a reaction of the mixture liquid at a temperature of 20-100° C. for 0.5-3 hours; undertake an appropriate solid-liquid separation process to remove the solvent and separate the solid from the liquid mixture. It is preferred: the reaction temperature is within 30-80° C., and the reaction time is within 1-2 hours. The solid-liquid separation process may be realized by a filtering method, a centrifugal method, a decantation method, or the like methods.

In Step S120, dry in an oven the solid that is obtained from the solid-liquid separation process to generate a titanium-containing silicon oxide material. The oven temperature ranges from 30 to 120° C., and the drying time ranges from 0.5 to 6 hours. It is preferred: the oven temperature is within 50-100° C., and the drying time is within 1 to 4 hours. In an anhydrous state, the obtained titanium-containing silicon oxide material is expressed by Formula (I):

$$xTiO_2(1-x)SiO_2 \qquad (I)$$

wherein x is a number within 0.002-0.2.

The titanium-containing silicon oxide material of the present invention can function as a catalyst. In one embodiment, calcination and/or silylation is undertaken to decrease the quantity of silanol groups, reduce the intrinsic acidity of the catalyst, and improve the surface property of the catalyst, whereby the catalytic activity of the catalyst is enhanced.

Step S130 is an optional procedure. In Step S130, undertake calcination of the titanium-containing silicon oxide material at a temperature of 300-800° C. for 1-9 hours, preferably at a temperature of 350-650° C. for 3-6 hours.

Step S140 is also an optional procedure. In Step S140, undertake silylation of the titanium-containing silicon oxide material. In one embodiment, one or more types of organic silanes and an ordinary method are used to realize the silylation.

The organic silane used to realize the silylation may be but is not limited to be selected from a group including halogenosilanes (having a general formula $R^1R^2R^3SiX$), silazanes (having a general formula $[R^4R^5R^6Si]_2NH$), methylsilane-imidazoles (having a general formula $R^7R^8R^9Si[N_2C_3H_3]$) and methylsilane-amines (having a general formula $(R^{10})_3SiN(R^{11})_2$), wherein $R^1$, $R^2$ and $R^3$ are identical or different, and each of $R^1$, $R^2$, and $R^3$ is a saturated alkyl group having 1-6 carbon atoms or a saturated phenyl group having 1-6 carbon atoms, and wherein $R^4$, $R^5$ and $R^6$ are identical or different, and each of $R^4$, $R^5$ and $R^6$ is an alkyl group having 1-6 carbon atoms, a haloalkyl group having 1-6 carbon atoms, or a phenyl group having 1-6 carbon atoms, and wherein each of $R^7$-$R^{11}$ is a saturated alkyl group having 1-3 carbon atoms. The preferred organic silane is selected from a group including hexamethyldisilazane, silylamines, trimethylsilyl chloride, n-(trimethylsilyl)-imidazol, and combinations thereof. The solvent used in silylation may be but is not limited to be selected from a group including aromatic hydrocarbon compounds having 6-16 carbon atoms, saturated alkanes having 6-16 carbon atoms, and combinations thereof. The preferred solvent is selected from a group including toluene, benzene, cyclohexane, isopropylbenzene, and combinations thereof.

In the silylation, the weight ratio of organic silane to titanium-containing silicon oxide material is within 0.01-1, preferably within 0.1-0.8; the weight ratio of solvent to titanium-containing silicon oxide material is within 1-200, preferably within 1-100. The reaction temperature of silylation is within 25-200° C., preferably within 50-150° C. The reaction time of silylation is within 0.5-3 hours, preferably within 1-2 hours.

Step S150 is also an optional procedure. In Step S150, incorporate a transition metal into the titanium-containing silicon oxide material.

Dependent on requirement, a transition metal may be incorporated into the titanium-containing silicon oxide material with an impregnation method, a precipitation method, a blending method, or another like method. In the impregnation method, a solution of a transition metal is dispersed in an appropriate solvent to form a mixture solution, and the mixture solution is further mixed with the titanium-containing silicon oxide material to form a titanium-containing silicon oxide material impregnated with the transition metal. Dependent on requirement, the titanium-containing silicon oxide material impregnated with the transition metal may be further dried and calcined. The concentration of the transition metal in the titanium-containing silicon oxide material is within 0.01-10 wt %, preferably within 0.05-5 wt %. The transition metal is inside or outside the skeletons of the titanium-containing silicon oxide material impregnated with the transition metal.

Figure 2:
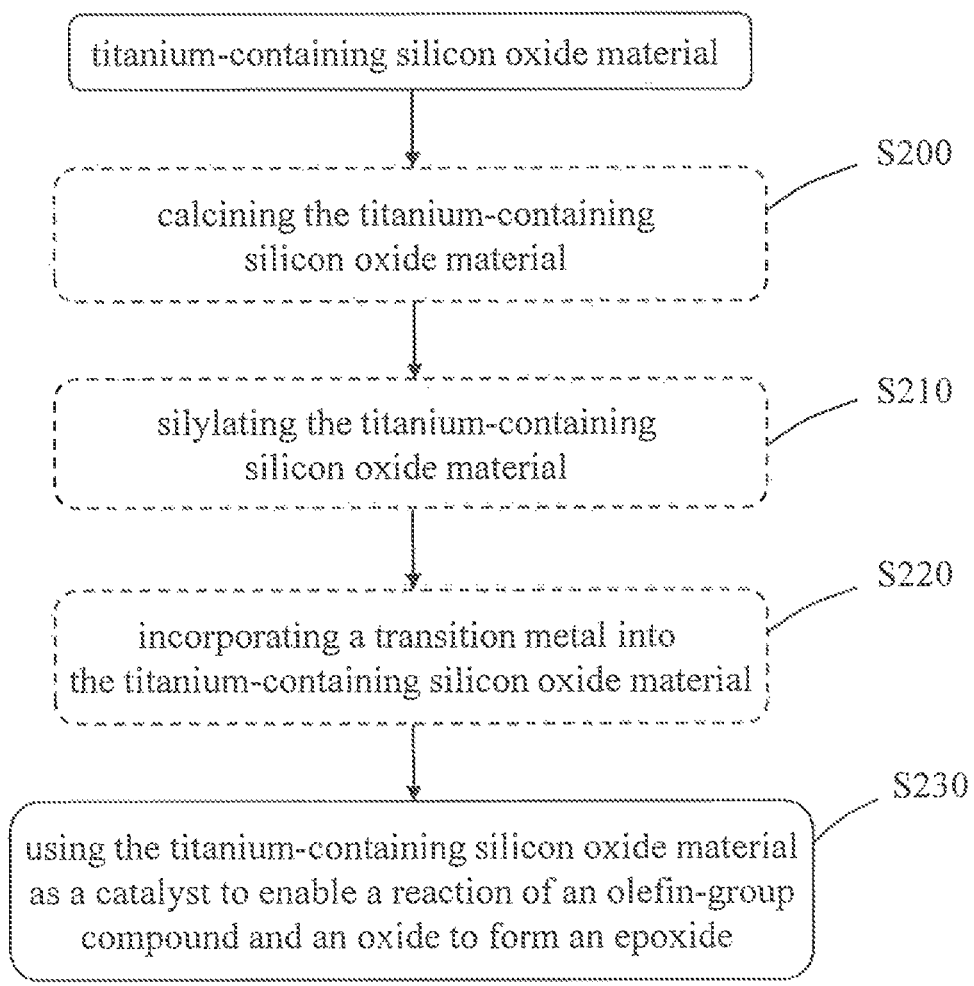
FIG. 2 is a flowchart of a method for fabricating an epoxide according to one embodiment of the present invention.

Refer to FIG. 2 a flowchart of a method using the titanium-containing silicon oxide material fabricated with the abovementioned method to fabricate an epoxide according to one embodiment of the present invention. There are four steps in the flowchart of FIG. 2, including Steps S200-S230. Step S230 describes the procedure to fabricate an epoxide. Step S200, Step S210 and Step S220 are the steps that may be added to the process of fabricating an epoxide to enhance the catalytic activity of the catalyst. In practical application, a single fabrication process can adopt one or more of Step S200, Step S210, and Step S220. However, the three optional steps are jointly presented in a single flowchart to simplify the diagram, and the dash-line frames indicate that the steps are optional.

Before the catalytic reaction of the present invention, the catalytic activity of the catalyst can be enhanced via undertaking calcination, silylation, and/or transition metal impregnation of the titanium-containing silicon oxide material, such as Step S200, Step S210, and/or Step S220 in FIG. 2. The technical details of Step S200, Step S210, and Step S220 are the same as Step S130, Step S140, and Step S150 and will not repeat herein.

In Step S230, use the titanium-containing silicon oxide material as the catalyst to catalyze the epoxidation reaction of olefin and oxide to form an epoxide.

The titanium-containing silicon oxide material used in the epoxidation reaction may be in form of powder, agglomerates, micro-spheres, or a single block. The titanium-containing silicon oxide material can be shaped via squeezing, compressing, or another appropriate method. The olefin-group compound used in the epoxidation reaction may be but is not limited to be selected from a group including aliphatic compounds, cyclic compounds (further including monocyclic compounds, bicyclic compounds and polycyclic compounds), mono-olefin compounds, di-olefin compounds, and poly-olefin compounds. While the quantity of the double bonds of the olefin-group compound is greater than 2, the double bonds may be conjugated double bonds or non-conjugated double bonds. The mono-olefin compounds may be but is not limited to be the olefin-group compounds having 2-60 carbon atoms and allowed to have a substitute radical, preferably a relatively-stable substitute radical. The mono-olefin compounds may be but is not limited to be selected from a group including ethylene, propylene, 1-butene, isobutene, 1-hexene, 2-hexene, 3-hexene, 1-octene, 1-decene, styrene, and cyclohexene. The di-olefin compounds may be but is not limited to be butadiene or isoprene.

The oxide used in the epoxidation reaction may be but is not limited to be an organic peroxide having a general formula: R—O—O—H, wherein R denotes an alkyl radical having 3-20 carbon atoms (preferably 3-10 carbon atoms). The alkyl radical may be but is not limited be a secondary alkyl group, a tertiary alkyl group, or an aralkyl group, such as the tertiary butyl group, the tertiary pentyl group, the cyclopentane group, or the 2-phenyl-2-propyl group. The organic peroxide may be but is not limited to be ethylbenzene hydroperoxide, cumene hydroperoxide, tertiary butyl hydroperoxide, or cyclohexyl hydroperoxide. While cumene hydroperoxide is used as the organic peroxide, the product of the reaction is alpha-Cumyl alcohol. Alpha-Cumyl alcohol can be converted into alpha-methyl styrene via dehydration. In addition to many applications in the industry, alpha-methyl styrene can be hydrogenated into cumene, which is the precursor of cumene hydroperoxide. The other organic peroxides also have the similar characteristic.

The oxide used in the epoxidation reaction may also be hydrogen peroxide having a general formula: H—O—O—H. Hydrogen peroxide may be in form of an aqueous solution and reacts with olefin to generate epoxide and water.

The oxide functioning as a reactant may be a concentrated/diluted pure/impure material.

In one embodiment, a solvent or diluent is added to the epoxidation reaction to make the reaction undertake in a liquid state. The solvent or diluent is in a liquid state in the environment of the epoxidation reaction and inert to all the reactants and products. The abovementioned solvent may be but is not limited to be ethylbenzene, cumene, isobutene, cyclohexene, or a combination thereof. The abovementioned solvent may be a material existing in the solution of the oxide to be used in the reaction. For example, while the cumene solution of cumene peroxide and an oxide is used as the oxide of the reaction, the cumene itself can function as the solvent, and addition of another solvent is unnecessary in such a case.

In the abovementioned method, the present invention does not strictly limit the quantity of the catalyst as long as the quantity of the catalyst is sufficient to make the epoxidation reaction fully completed in the shortest time. In the epoxidation reaction, the molar ratio of olefin to oxide ranges from 1:100 to 100:1, preferably from 1:10 to 10:1. The present invention does not particularly limit the reaction temperature of the epoxidation reaction. The reaction temperature is normally within 0-200° C., preferably within 25-150° C. The present invention does not particularly limit the reaction pressure of the epoxidation reaction as long as the reaction pressure is greater than the pressure keeping all the reactants in a liquid state. The reaction pressure is preferably within 1-100 atm. The reaction time of the epoxidation reaction ranges from 1 minute to 48 hours, preferably from 5 minutes to 8 hours. The epoxidation reaction can be undertaken in batches, continuously, or semi-continuously in various types of reactors and instruments, such as fixed bed reactors, transport bed reactors, fluid bed reactors, slurry reactors, and continuously-stirred tank reactors.

Below, embodiments are used to demonstrate how the present invention fabricates a titanium-containing silicon oxide material and uses the material as a catalyst to catalyze the epoxidation reaction of olefin and oxide and generate an epoxide.

Embodiment I

Fabrication of a Titanium-Containing Silicon Oxide Material:

Add 6.1 g tetraisopropylorhotitanate to 178.6 g isopropyl alcohol to form a first solution. Add 48.5 g silica gel (sourced from Sigma-Aldrich 236772) to the first solution, and mix them uniformly to form a second solution, wherein the silica gel has a pore diameter of 6 nm, a specific surface area of 500 m$^2$/g, and a particle diameter of 35-75 μm. Next, agitate the second solution at a temperature of 80° C. for 2 hours to obtain a first suspension. Next, filter the first suspension to remove the solvent and obtain a first powder. Next, dry the first powder at a temperature of 70° C. for less than 2 hours. Next, heat the dried first powder at a temperature rise rate of 3° C./minute to a temperature of 500° C., and hold the first powder at the temperature of 500° C. for 5 hours to calcine the first powder. Next, let the first powder cool down naturally.

Fabrication of Propylene Epoxide:

Use 16.5 g titanium-containing silicon oxide material fabricated in Embodiment I as the catalyst and undertake a silylation reaction of the catalyst. Mix the catalyst with 165 g toluene and 11.2 g hexamethyldisilazane uniformly to form a third solution. Next, agitate the third solution at a temperature of 120° C. for 1 hour to obtain a second suspension. Next, filter the second suspension to obtain a second powder as the catalytic material. Next, dry the catalytic material. Next, uniformly mix the catalytic material, 225 g of a 25 wt % hydrogen peroxide cumene solution (cumene is the solvent), and 125 g propylene in a 1-liter airtight autoclave, and undertake a reaction at a temperature of 85° C. for less than 1.5 hours. The result of the reaction is shown in Table. 1.

Embodiment II

Fabrication of a Titanium-Containing Silicon Oxide Material:

The process for fabricating a titanium-containing silicon oxide material is the same as Embodiment I except Embodiment II is free of the calcination process.

Fabrication of Propylene Epoxide:

Use the titanium-containing silicon oxide fabricated in Embodiment II as the catalyst, and the succeeding process is the same as Embodiment I except Embodiment II does not undertake the silylation reaction of the catalyst. The result of the reaction is shown in Table. 1.

Embodiment III

Fabrication of a Titanium-Containing Silicon Oxide Material:

The process for fabricating a titanium-containing silicon oxide material is the same as Embodiment I except Embodiment III is free of the calcination process.

Fabrication of Propylene Epoxide:

Use the titanium-containing silicon oxide fabricated in Embodiment III as the catalyst, and the succeeding process is the same as Embodiment I. The result of the reaction is shown in Table. 1.

Embodiment IV

Fabrication of a Titanium-Containing Silicon Oxide Material:

The process for fabricating a titanium-containing silicon oxide material is the same as Embodiment I.

Fabrication of Propylene Epoxide:

Use the titanium-containing silicon oxide fabricated in Embodiment IV as the catalyst, and the succeeding process is the same as Embodiment I except Embodiment IV does not undertake the silylation reaction of the catalyst. The result of the reaction is shown in Table. 1.

Embodiment V

Fabrication of a Titanium-Containing Silicon Oxide Material:

The process for fabricating a titanium-containing silicon oxide material is the same as Embodiment I except using 33.6 g silica gel, 5.1 g tetra isopropyl titanate, and 100 g isopropyl alcohol, wherein the silica gel is sourced from Sigma-Aldrich 236810, having a pore diameter of 15 nm, a specific surface area of 300 m$^2$/g, and a particle diameter of 35-75 μm.

Fabrication of Propylene Epoxide:

Use the titanium-containing silicon oxide fabricated in Embodiment V as the catalyst, and the succeeding process is the same as Embodiment I. The result of the reaction is shown in Table. 1.

Embodiment VI

Fabrication of a Titanium-Containing Silicon Oxide Material:

The process for fabricating a titanium-containing silicon oxide material is the same as Embodiment I except using 12.1 g silica gel, 2 g tetra isopropyl titanate, and 59 g isopropyl alcohol, wherein the silica gel is sourced from Oriental Silicas Corporation TXR-120-2, having a specific surface area of 680-760 m$^2$/g.

Fabrication of Propylene Epoxide:

Use 7.5 g titanium-containing silicon oxide material fabricated in Embodiment VI as the catalyst, and undertake a silylation reaction of the catalyst. The succeeding process is the same as Embodiment I. The result of the reaction is shown in Table. 1.

Embodiment VII

Fabrication of a Titanium-Containing Silicon Oxide Material:

Add 2.1 g tetraisopropylorhotitanate to 298 g isopropyl alcohol, and agitate them at an ambient temperature to form a fourth solution. Add 16.2 g silica gel (sourced from Sigma-Aldrich 236802) to 298 g isopropyl alcohol at a temperature of 80° C., and agitate them to form a fifth solution, wherein the silica gel has a pore diameter of 6 nm, a specific surface area of 500 m$^2$/g, and a particle diameter of 250-500 μm. Next, mix the fourth solution and the fifth solution at a temperature of 80° C., and agitate them persistently for 2 hours to form a third suspension. Next, filter the third suspension to remove the solvent and obtain a third powder. Next, dry the third powder at a temperature of 70° C. for less than 2 hours. Next, heat the dried third powder at a temperature rise rate of 3° C./minute to a temperature of 500° C., and hold the first powder at the temperature of 500° C. for 5 hours to calcine the third powder. Next, let the third powder cool down naturally.

Fabrication of Propylene Epoxide:

Use 7.5 g titanium-containing silicon oxide material fabricated in Embodiment VII as the catalyst, and undertake a silylation reaction of the catalyst. Mix the catalyst with 75 g toluene and 5.1 g hexamethyldisilazane uniformly to form a sixth solution. Next, agitate the sixth solution at a temperature of 120° C. for 1 hour to obtain a fourth suspension. Next, filter the fourth suspension to obtain a fourth powder as the catalytic material. Next, dry the catalytic material. Next, uniformly mix the catalytic material, 225 g of a 25 wt % hydrogen peroxide cumene solution (cumene is the solvent), and 125 g propylene in a 1-liter airtight autoclave, and undertake a reaction at a temperature of 85° C. for less than 1.5 hours. The result of the reaction is shown in Table. 1.

TABLE 1

| | E1 (Note 3) | E2 | E3 | E4 | E5 | E6 | E7 |
|---|---|---|---|---|---|---|---|
| Conversion rate of hydrogen peroxide cumene (%) (Note 1) | 98 | 49 | 91 | 53 | 96 | 86 | 88 |
| Selection rate of propylene epoxide (%) (Note 2) | >97 | >73 | >96 | >73 | >96 | >97 | >96 |

(Note 1): conversion rate of hydrogen peroxide cumene = consumed quantity of hydrogen peroxide cumene/added quantity of hydrogen peroxide cumene × 100%.
(Note 2): selection rate of propylene epoxide = generated quantity of propylene epoxide/consumed quantity of hydrogen peroxide cumene × 100%.
(Note 3): E denotes an embodiment.

Table. 1 shows that the method for fabricating titanium-containing silicon oxide material of the present invention is applied to various types of amorphous silicon dioxide carriers respectively having different physical properties. The titanium-containing silicon oxide material has a catalytic effect on the epoxidation reaction. Further, the catalytic activity of the titanium-containing silicon oxide material can be enhanced via calcination and/or silylation.

In conclusion, the present invention proposes a method for fabricating a titanium-containing silicon oxide material, which is exempted from using a template to fabricate a titanium-containing silicon oxide material and thus able to significantly simplify the process of fabricating a titanium-containing silicon oxide material. The titanium-containing silicon oxide material fabricated by the method has a superior catalytic activity, able to function as a catalyst to successfully catalyze an epoxidation reaction of olefin-group compounds and effectively increase the yield of epoxide. The present invention also proposes an application using the titanium-containing silicon oxide material fabricated by the method.

The present invention has been demonstrated in detail with the embodiments above. However, these embodiments are only to exemplify the present invention but not to limit the scope of the present invention. Any equivalent modification or variation according to the characteristic or spirit of the present invention is to be also included within the scope of the present invention.

What is claimed is:

1. A method for fabricating a titanium-containing silicon oxide material, comprising steps:
   preparing a mixture liquid containing an amorphous silicon dioxide, a titanium source and a solvent;
   enabling a reaction of said mixture liquid without using a template, and undertaking a solid-liquid separation process; and
   drying a solid-state material obtained in said solid-liquid separation process to obtain a titanium-containing silicon oxide material, wherein in an anhydrous state, said titanium-containing silicon oxide material is expressed by Formula (I):

$$x\mathrm{TiO}_2(1-x)\mathrm{SiO}_2 \qquad (I)$$

wherein x is a number within 0.002-0.2.

2. The method according to claim 1, wherein said amorphous silicon dioxide is smoked silica, fumed silica, silica gel, or silica sol; said titanium source is a titanate or an inorganic titanium source; said solvent is an alcohol-group compound.

3. The method according to claim 2, wherein said titanate is selected from a group consisting of tetramethyl titanate, tetraethyl titanate, tetrapropyl orthotitanate, tetra isopropyl titanate, tetrabutyl orthotitanate, tetra sec-butyl titanate, tetrabutyl isotitanate, tetra tert-butyl titanate, and combinations thereof; said inorganic titanium source is titanium trichloride or titanium tetrachloride; said solvent is selected from a group consisting of methyl alcohol, ethyl alcohol, isopropyl alcohol, butyl alcohol, and tert-butyl alcohol.

4. The method according to claim 1, wherein a molar ratio of titanium to silicon ranges from 0.002 to 0.2.

5. The method according to claim 4, wherein a molar ratio of titanium to silicon ranges from 0.01 to 0.1.

6. The method according to claim 1, wherein said reaction of said mixture liquid is undertaken at a temperature of 20-100° C. for 0.5-3 hours; said solid-state material obtained in said solid-liquid separation process is persistently dried at a temperature of 30-120° C. for 0.5-6 hours.

7. The method according to claim 1 further comprising at least one of following steps:
   calcining said titanium-containing silicon oxide material at a temperature of 300-800° C. for 1-9 hours;
   silylating said titanium-containing silicon oxide material at a temperature of 25-200° C. for 0.5-3 hours; and
   incorporating a transition metal into said titanium-containing silicon oxide material, wherein a concentration of said transition metal in said titanium-containing silicon oxide material is within 0.01-10 wt %.

8. The method according to claim 7, wherein said concentration of said transition metal in said titanium-containing silicon oxide material is within 0.05-5 wt %.

9. A method for fabricating an epoxide, comprising a steps:
providing said titanium-containing silicon oxide material fabricated according to claim 1 as a catalyst to enable a reaction of an olefin-group compound and an oxide to form an epoxide.

10. The method according to claim 9, wherein said olefin-group compound is a mono-olefin compound, a di-olefin compound, or a poly-olefin compound; said oxide is an organic peroxide or a hydroperoxide.

11. The method according to claim 10, wherein said mono-olefin compound is selected from a group consisting of ethylene, propylene, 1-butene, isobutene, 1-hexene, 2-hexene, 3-hexene, 1-octene, 1-decene, styrene, and cyclohexene; said di-olefin compound is butadiene or isoprene; said organic peroxide is ethylbenzene hydroperoxide, cumene hydroperoxide, tertiary butyl hydroperoxide, or cyclohexyl hydroperoxide.

12. The method according to claim 9, wherein a molar ratio of said olefin-group compound to said oxide ranges from 1:100 to 100:1.

13. The method according to claim 12, wherein said molar ratio of said olefin-group compound to said oxide ranges from 1:10 to 10:1.

14. The method according to claim 9, wherein said reaction of said olefin-group compound and said oxide is undertaken for 1 minute-48 hours at a temperature of 0-200° C. and at a pressure of 1-100 atm.

15. The method according to claim 14, wherein said reaction of said olefin-group compound and said oxide is undertaken for 5 minute-8 hours at a temperature of 25-150° C. and at a pressure of 1-100 atm.

* * * * *